United States Patent
Zelten et al.

(10) Patent No.: US 8,535,257 B1
(45) Date of Patent: Sep. 17, 2013

(54) SYRINGE AND SWAB SYSTEM

(76) Inventors: Michael S. Zelten, Oklahoma City, OK (US); Keith Ronald Brown, Edmond, OK (US)

( * ) Notice: Subject to any disclaimer, the term of this patent is extended or adjusted under 35 U.S.C. 154(b) by 0 days.

(21) Appl. No.: 13/135,088

(22) Filed: Jun. 24, 2011

Related U.S. Application Data

(60) Provisional application No. 61/399,116, filed on Jul. 7, 2010.

(51) Int. Cl.
*A61F 13/38* (2006.01)
*A61M 5/42* (2006.01)

(52) U.S. Cl.
USPC ............................. 604/1; 604/192

(58) Field of Classification Search
USPC .................................. 604/1–3, 192
See application file for complete search history.

(56) References Cited

U.S. PATENT DOCUMENTS

| | | | | |
|---|---|---|---|---|
| 2,627,269 A * | 2/1953 | McGregor | 604/2 |
| 3,270,743 A * | 9/1966 | Gingras | 604/192 |
| 3,658,061 A * | 4/1972 | Hall | 604/263 |
| 3,680,559 A * | 8/1972 | Gorbahn | 604/193 |
| 3,977,401 A * | 8/1976 | Pike | 604/144 |
| 4,243,035 A * | 1/1981 | Barrett | 604/1 |
| 4,635,633 A * | 1/1987 | Hufnagle | 606/181 |
| 4,735,617 A * | 4/1988 | Nelson et al. | 604/192 |
| 4,735,618 A * | 4/1988 | Hagen | 604/192 |
| 4,799,926 A * | 1/1989 | Haber | 604/187 |
| 4,867,746 A * | 9/1989 | Dufresne | 604/192 |
| 4,883,469 A * | 11/1989 | Glazier | 604/192 |
| 4,886,503 A * | 12/1989 | Miller | 604/192 |
| 4,915,698 A * | 4/1990 | Levenson | 604/192 |
| 4,929,241 A * | 5/1990 | Kulli | 604/263 |
| 4,982,842 A * | 1/1991 | Hollister | 206/365 |
| 5,053,017 A * | 10/1991 | Chamuel | 604/192 |
| 5,055,102 A * | 10/1991 | Sitnik | 604/192 |
| 5,078,693 A * | 1/1992 | Shine | 604/192 |
| 5,092,461 A * | 3/1992 | Adam | 206/365 |
| 5,112,311 A * | 5/1992 | Utterberg et al. | 604/177 |
| 5,135,509 A * | 8/1992 | Olliffe | 604/192 |
| 5,151,089 A * | 9/1992 | Kirk et al. | 604/192 |
| 5,188,611 A * | 2/1993 | Orgain | 604/192 |
| 5,190,521 A * | 3/1993 | Hubbard et al. | 604/512 |
| 5,192,270 A * | 3/1993 | Carswell, Jr. | 604/116 |
| 5,197,954 A * | 3/1993 | Cameron | 604/110 |
| 5,242,417 A * | 9/1993 | Paudler | 604/192 |
| 5,312,367 A * | 5/1994 | Nathan | 604/192 |
| 5,332,092 A * | 7/1994 | Fischer | 206/365 |
| 5,342,320 A * | 8/1994 | Cameron | 604/192 |
| 5,669,889 A * | 9/1997 | Gyure et al. | 604/263 |
| 5,713,874 A * | 2/1998 | Ferber | 604/198 |
| 5,836,920 A * | 11/1998 | Robertson | 604/192 |
| 5,961,494 A * | 10/1999 | Hogan | 604/191 |
| 5,989,229 A * | 11/1999 | Chiappetta | 604/263 |
| 5,993,426 A * | 11/1999 | Hollister | 604/192 |
| 6,540,696 B1 * | 4/2003 | Dillon et al. | 600/573 |
| 6,719,737 B2 * | 4/2004 | Kobayashi | 604/263 |
| 7,393,345 B2 * | 7/2008 | Yang | 604/199 |
| 7,794,675 B2 * | 9/2010 | Lynn | 422/294 |
| 8,167,847 B2 * | 5/2012 | Anderson et al. | 604/187 |
| 2005/0187493 A1 * | 8/2005 | Swenson et al. | 600/576 |
| 2007/0167917 A1 * | 7/2007 | Lee | 604/187 |
| 2011/0295207 A1 * | 12/2011 | Brugger et al. | 604/164.04 |

* cited by examiner

*Primary Examiner* — Melanie Hand
*Assistant Examiner* — Paula Craig
(74) *Attorney, Agent, or Firm* — Martin G. Ozinga; Phillips Murrah PC

(57) ABSTRACT

The current invention is a syringe and swab system for a syringe having a plunger, a barrel, a needle hub, a needle, a needle safety cover, and a swab attached to the distal end of the needle safety cover for placing over an injection site to apply pressure.

9 Claims, 3 Drawing Sheets

SYRINGE AND SWAB SYSTEM

CROSS-REFERENCE TO RELATED APPLICATIONS

Priority is claimed from provisional patent application U.S. Ser. No. 61/399,116 filed on Jul. 7, 2010 and incorporated by reference herein.

1. FIELD OF THE INVENTION

The present invention relates generally to syringes and swabs associated with hypodermic injections. More particularly, the present invention is a new and improved syringe and swab system that provides an absorbent swab generally fixed to a syringe needle safety cover such as but not limited to a BD ECLIPSE NEEDLE.

2. DESCRIPTION OF THE KNOWN PRIOR ART

Although hypodermic injections and associated syringe therewith are well known and have been utilized for over 100 years, the medical profession is constantly trying to improve the device and process to make it easier for the medical professional, safer for the patient, and safer for the medical professional. The process has not really changed over the years where it is still necessary to provide a swab for removing blood and excess fluid from the injection site after removal of the needle as well as to apply pressure to the site of the injection to stop bleeding and leaking of fluid in general.

It is frequently the bane of the medical professional giving the injection to find a gauze pad or swab while fumbling with the used needle after the injection. It is common that the injection is performed before the professional realizes that a swab is not handy, out of supply, or found and applied too slow when fluid such as blood may sometimes squirt after the needle is removed from the injection site. The prior art is lacking an adequate means for a readily available and handy swab for post injection with a needle that can always be available as part of the injection process.

Furthermore, it is also obviously desirable to provide a safe and reliable means for discarding a used needle which may be contaminated with undesirable fluid and biomaterials in general. Numerous devices have been utilized for re-covering or re-capping a needle from a syringe before discarding to lessen and hopefully prevent "sticks" to the medical professional handling the used needle either trying to recap the needle or dispose of in general.

A known prior art device is the is a syringe needle safety cover such as the BD ECLIPSE NEEDLE depicted in the illustrations. The device generally allows for a guard to be snapped in over the needle after use with a finger or thumb from below the point of the needle thereby decreasing the chances of an errant "stick" and removing the need to re-cap the needle. This is essentially accomplished by a hinged protective cover that can be pushed or rotated up at the base of the needle or needle hub. When the cover is snapped over the needle, as in the illustration, the cover is generally locked into place forming a cohesive body with the syringe barrel, needle hub, and needle.

Although numerous advancements have occurred with needles and safety, the prior art still has failed to bridge the gap between syringes and medical professional demand and needs for post injection swaps. Therefore, an extensive opportunity for design advancements and innovation remains where the prior art fails or is deficient.

SUMMARY OF THE INVENTION

In general, the present invention is a new and improved syringe and swab system which provides a protective cover or shield to a used needle and provides a swab for excess fluid and applying pressure to the injection site where the prior art fails. The present invention generally provides a sterile swab attached to syringe wherein a readily available system is provided for the injection and post injection needs.

Without the intention of limitation, the invention may generally comprise an attachment to a needle cover generally used to dispose of the needle in a safe manner. The attachment may generally be located on the needle system and sterilized along with the needle, pre-use needle cover, and post use needle cover. The attachment may be removably or permanently attached and have a swab, gauze, foam or other absorbent material whereby the syringe may be utilized after use to hold pressure and absorb after the needle is removed from the patient and the safety cover is placed over the needle.

In this respect, before explaining at least one embodiment of the invention in detail, it is to be understood that the invention is not limited in this application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

Accordingly, titles, headings, chapter names, classifications and overall segmentation of the application in general should not be construed as limiting. Such are provided for overall readability and not necessarily as literally defining text or material associated therewith.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved syringe and swab system that provides greater ease, safety, and function to a wide range of uses associated with the utilization of syringes and post injection swab applications.

It is a further object of the present invention to provide a new and improved syringe and swab system which is of a relatively simple design and thus may be easily and efficiently manufactured.

An even further object of the present invention is to provide a new and improved syringe and swab system which is of a more durable and reliable construction than that of the existing known art.

Still another object to the present invention is to provide a new and improved syringe and swab system which is susceptible of a low cost of manufacture with regard to both materials and labor, which accordingly is then susceptible of low prices of sale to the consuming public, thereby making such economically available to those utilizing syringes.

Another object of the present invention is to provide a new and improved syringe and swab system which provides some of the advantages of the prior art, while simultaneously overcoming some of the disadvantages normally associated therewith.

Yet another object of the present invention to provide a new and improved syringe and swab system that covers a used needle while also providing an absorbent material that may be utilized post injection.

Still further, it is an object of the present invention to provide a new and improved syringe and swab system that will allow the medical professional to always have a readily available swab after an injection without the need for a separate swab.

It is a further object of the present invention to provide a new and improved syringe and swab system which is of a relatively simple design and thus may be easily and efficiently manufactured with a needle such as but not limited to the to a syringe needle safety cover such as the BD ECLIPSE NEEDLE.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference would be had to the accompanying drawings and descriptive matter in which there are illustrated preferred embodiments of the invention.

BRIEF DESCRIPTION OF THE DRAWINGS AND PICTORIAL ILLUSTRATIONS

The invention will be better understood and objects other than those set forth above will become apparent when consideration is given to the following detailed description thereof. Such description makes reference to the annexed pictorial illustrations, graphs, drawings, drawings, and appendices.

DETAILED DESCRIPTION OF THE PREFERRED EMBODIMENTS

Figure 1:
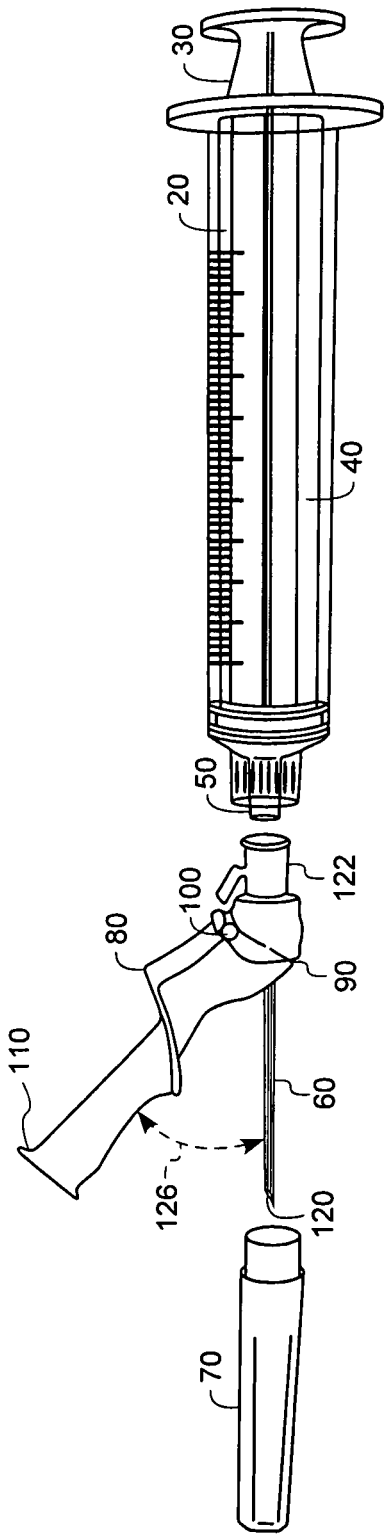
FIG. 1 is a general depiction of a prior art device with a hinged needle guard.
Figure 2:
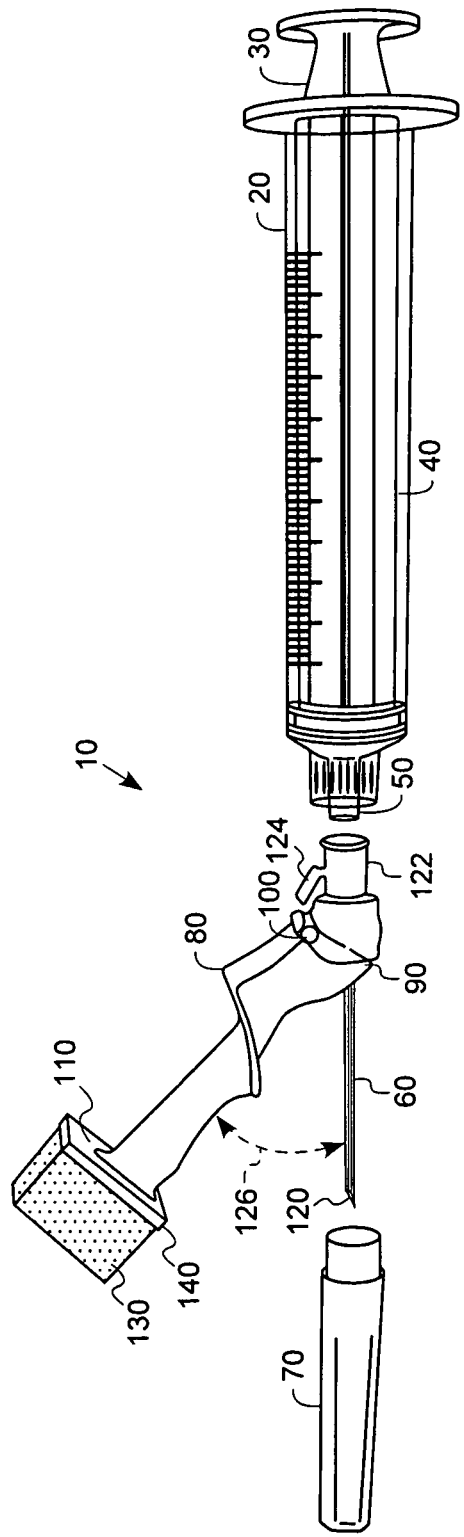
FIG. 2 is a general depiction of a preferred embodiment of the invention illustrating a syringe and swab system with a protective cap detached from the needle and hinged needle guard with swab.
Figure 3:
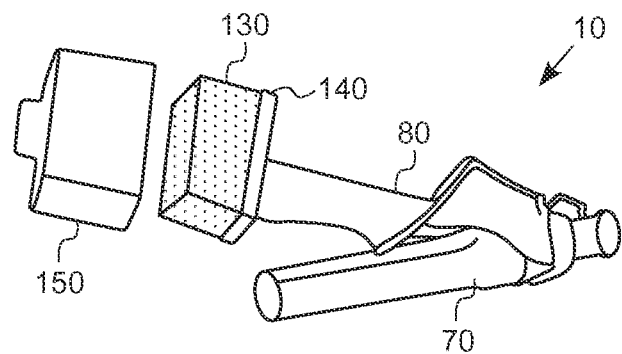
FIG. 3 is a general depiction of a preferred embodiment of the invention illustrating the needle with a protective cap on and the hinged needle guard with a cap for a swab.
Figure 4:
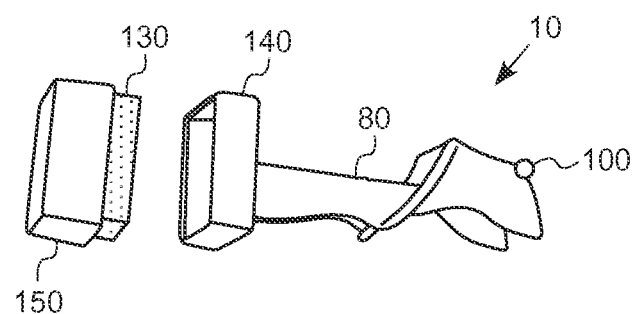
FIG. 4 is a general depiction of a preferred embodiment of the invention illustrating the needle guard with a swab in the cap detached from the guard.
Figure 5:
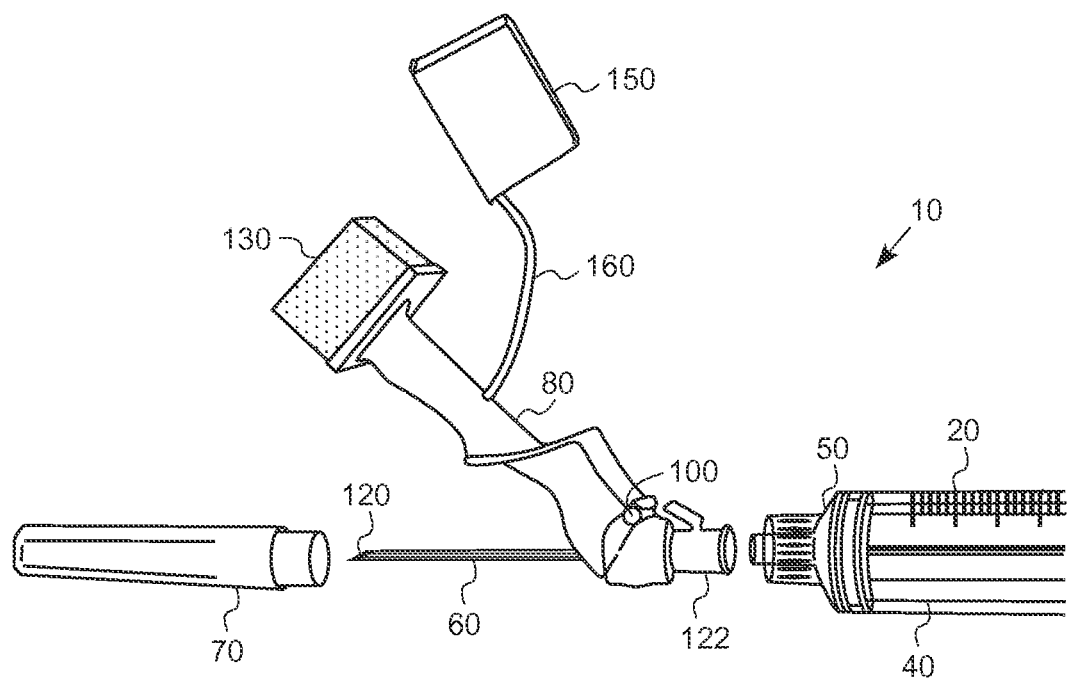
FIG. 5 is a general depiction of a preferred embodiment of the invention illustrating the needle guard with a swab and cap wherein the cap is attached to the guard and the syringe is only partially depicted.

Referring now to the drawings, wherein like reference numerals designate corresponding structure throughout the views, and referring in particular to FIG. 1, reference numeral 10 generally refers to a new and improved syringe and swab, syringe and swab system, method of use, and method of making hereinafter referred to as "invention 10", in accordance with a preferred embodiment.

A syringe 20 generally comprising a plunger 30, a barrel 40, a needle hub 50, and a needle 60. It is also common that syringe 20 needle hub 50 allows for attaching and detaching needle 60 although the current invention also contemplates syringe 20 with a fixed or non-removable needle 60. It is still further contemplated that invention 10 may be utilized on non-standard syringe 20 of multiple configurations or other applications where a needle, is used hypodermically.

Now referring to the illustrations and more in particular to FIG. 1, a prior art device is generally depicted. It is not unusual for needle 60 to have a protective cover or cap 70 for pre use safety and a protective guard 80 for post use safety and disposal of needle 60. It has been found that attempting to replace cap 70 after use of needle 60 lends to unnecessary punctures to medical professional and needle users in general. Therefore, numerous safety devices have been utilized to cover or guard used needle 60 such as the BD ECLIPSE NEEDLE system wherein protective guard 80 may be hingedly rotated or moved to cover needle 60 after use for disposal.

It is common for needle 60 to be sold and or packaged separately with cap 70 on needle 60 and then screwed on needle hub 50 when preparing for use. It is also common for protective guard 80 to be generally attached to needle 60 and rotated out of the way during the injection and then rotated to cover needle 60 after the injection. It is understood that the term "cover" may not literally mean needle 60 is totally encapsulated, but may mean that needle 60 is shielded to protect persons from an accidental puncture or "stick".

Guard 80 generally comprises a first end 90 attached toward syringe hub portion 50 of needle 60 such as but not limited to the BD ECLIPSE NEEDLE system wherein hinge 100 is utilized. Guard 80 also generally comprises a second or distal end 110 that generally covers needle 60 distal end 120.

Needle 60 distal end 120 is the point of insertion for syringe 20 whereas needle 60 connector 122 is typically made of plastic and screws or otherwise attaches to syringe hub portion 50. Typically, needle 60 connector 122 may have a receiver 124 that allows guard 80 to snap onto needle 60 connector 122 in a hinged fashion. Guard 80 may be positioned out of the way during insertion, but then swung generally along arc 126 such that needle 60 distal end 120 is covered after use for disposal. It is understood that the guard 80 may swing farther away from needle 60 than depicted in the illustrations when it is desired to have needle 60 clear of any obstruction while inserting needle 60. It is also known in the prior art to provide guard 80 such that it snaps over needle 60 wherein needle 60 is trapped in guard 80 such that needle is secured in guard 80.

Now referring to the illustration and more in particular to FIGS. 2 through 5, in a preferred embodiment, guard 80 distal end 110 may further comprise a pad 130 that may or may not be absorbent. Pad 130 may utilize gauze, swab, foam, and so forth found in the art for absorbing fluids and or generally to stop or reduce bleeding after an injection. It is also contemplated to provide a generally solid base 140 for pad 130 such that pad 130 may have pressure applied by the user by generally holding syringe 20. It is contemplated that pad 130 may be removably attached to distal end 110 of guard 80, base 140 may be removably attached to distal end 110 of guard 80, and or combinations thereof.

It is still further contemplated that invention 10 may include packaging of pad 130 with needle 60 with or without guard 80 attached to needle 60. It is contemplated that pad 130 and or base 140 may be sterile or sterilized with needle 60, guard 80, cap 70, and or combinations thereof. It is also contemplated that pad 130 may be treated with alcohol and or medication as desired. It is understood that pad 130 may have numerous other pretreatments applied.

Pad 130 may also utilize cover 150 wherein pad 130 is generally protected until use of pad 130 is desired. Cover 150 may be removably attached to base 140, pad 130, and combinations thereof. Cover 150 may include attachment 160 to guard 80. It is understood that numerous configuration may be utilized such as but not limited to more than one pad 130, with more than one cover 150 wherein first pad 130 may be utilized to apply an alcohol preparation before the injection and a second pad 130 utilized to apply pressure and absorb unwanted fluids after the injection.

Figure 6:
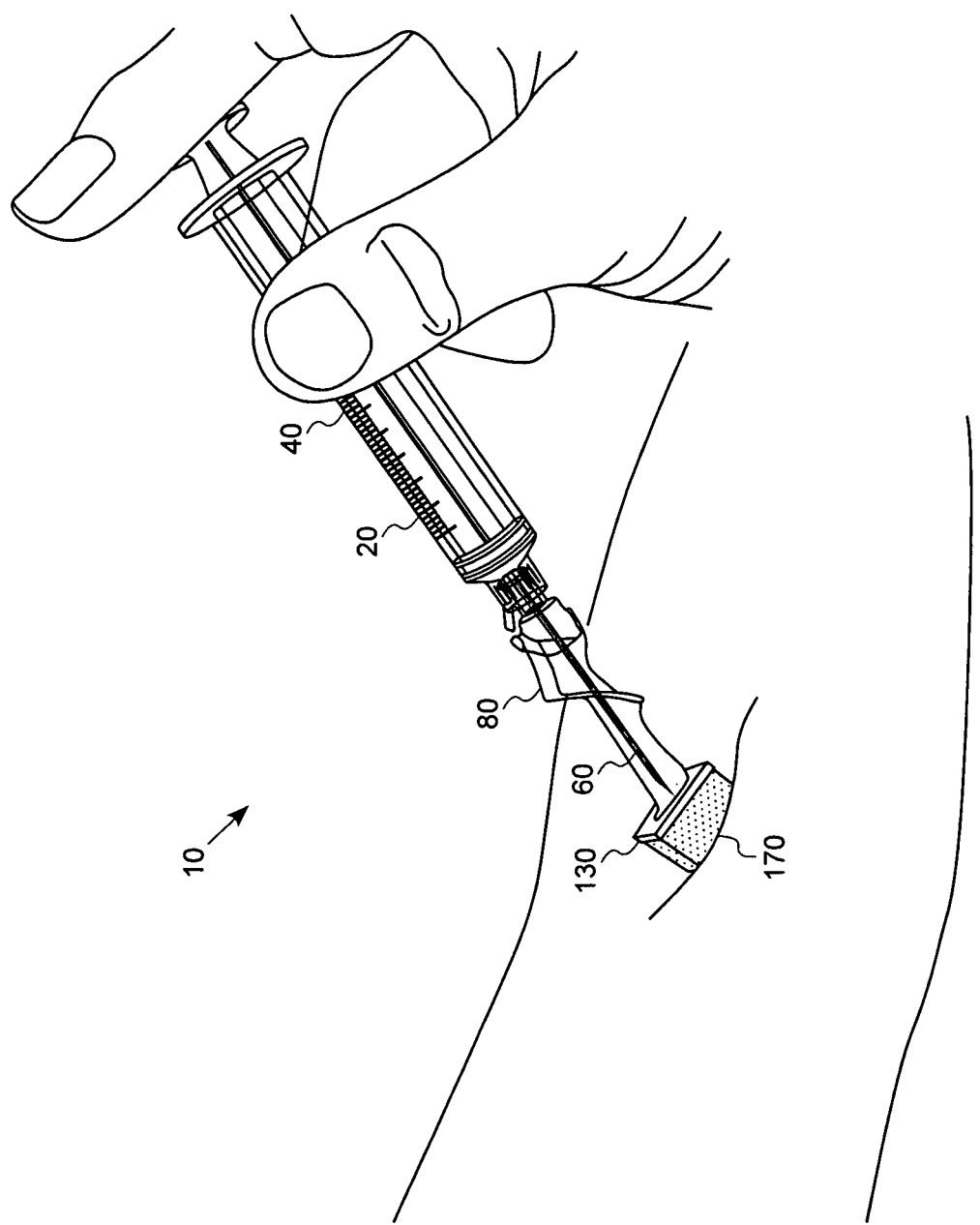
FIG. 6 is a general depiction of a preferred embodiment of the invention illustrating a syringe and swab system wherein a guard has been swung over a needle after the injection and a swab is being placed against the injection site by a user.

Again referring to the illustration and more in particular to FIG. 6, invention 10 is generally depicted wherein guard 80 has been snapped over needle 60 and pad 130 is being applied to the site of the injection. Guard 80 is generally aligned with syringe 20 such that pressure may be applied by holding syringe 20 against the injection point 170.

Furthermore, invention 10 is generally shown in a configuration for typical medical use for syringe having use with medicine or general fluid delivery hypodermically. It is understood that the invention 10 may be used in other applications such as but not limited to laboratory procedures, medical research, veterinary medicine and so forth where it is desired to apply post injection pressure and swab. It is further understood that invention 10 may be used on non medical applications. The term syringe should not be considered limited to applications normally associated with medical use. Still furthermore, the term syringe generally refers to a device which may hold fluid and then deliver fluid in measured amounts.

Accordingly, other implementations are within the scope of the following claims. Changes may be made in the combinations, operations, and arrangements of the various parts and elements described herein without departing from the spirit and scope of the invention.

We claim:

1. A needle guard system for covering a syringe needle after use, comprising:

a needle guard, said needle guard including a first end configured for attaching said needle guard to a syringe needle, and a distal end opposite the first end;

said needle guard including a swab portion, a protective guard portion, and a hinge;

said swab portion being located at the distal end of said needle guard, said hinge being located between said protective guard portion and the first end, and said protective guard portion being located between said hinge and said swab portion;

said needle guard being configured such that after use of the syringe needle, said protective guard portion swings at said hinge along an arc to cover the syringe needle, with the syringe needle being separated from said swab portion by said protective guard portion.

2. The needle guard system of claim 1, wherein said needle guard system further includes a removable cover for covering said swab portion.

3. The needle guard system of claim 2 wherein said swab removable cover is attached to said needle guard.

4. The needle guard system of claim 3 wherein said swab portion is made from foam.

5. A syringe and swab system for applying pressure and absorption to an injection site from a needle after an injection, comprising:

a syringe, the syringe having a plunger, a barrel, a needle hub, and a needle;

a needle guard, said needle guard including a first end and a distal end, the first end attaching said needle guard to said syringe, the distal end being opposite the first end;

said needle guard including a swab portion, a protective guard portion, and a hinge;

said swab portion being located at the distal end of said needle guard, said hinge being located between said protective guard portion and the first end, and said protective guard portion being located between said hinge and said swab portion;

said needle guard being configured such that after an injection, said protective guard portion swings at said hinge along an arc to cover said needle, with said needle being separated from said swab portion by said protective guard portion.

6. The syringe and swab system of claim 5, wherein said syringe and swab system further includes a removable cover for covering said swab portion.

7. The syringe and swab system of claim 6 wherein said swab removable cover is attached to said needle guard.

8. The syringe said swab portion system of claim 7 wherein said swab is made from foam.

9. The syringe and swab system of claim 8 wherein said swab portion is detachable from said protective guard portion.

* * * * *